(12) United States Patent
Fan

(10) Patent No.: US 8,613,135 B2
(45) Date of Patent: Dec. 24, 2013

(54) METHOD FOR NON-PLANAR CHIP ASSEMBLY

(75) Inventor: Long-Sheng Fan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/300,547

(22) Filed: Nov. 18, 2011

(65) Prior Publication Data

US 2012/0279060 A1 Nov. 8, 2012

Related U.S. Application Data

(63) Continuation-in-part of application No. 13/282,422, filed on Oct. 26, 2011, which is a continuation-in-part of application No. 13/102,596, filed on May 6, 2011.

(60) Provisional application No. 61/553,919, filed on Oct. 31, 2011.

(51) Int. Cl.
 *H05K 3/30* (2006.01)
(52) U.S. Cl.
 USPC .................. 29/832; 29/825; 29/830; 29/840
(58) Field of Classification Search
 USPC ................................ 29/825, 830, 832; 385/14
 See application file for complete search history.

(56) References Cited

U.S. PATENT DOCUMENTS

| | | | | |
|---|---|---|---|---|
| 5,650,363 | A * | 7/1997 | Endroes et al. | 438/57 |
| 6,294,831 | B1 * | 9/2001 | Shishido et al. | 257/729 |
| 7,113,661 | B2 * | 9/2006 | Arai et al. | 385/14 |
| 7,914,842 | B1 | 3/2011 | Greenberg et al. | |
| 2003/0160303 | A1 | 8/2003 | Hirokawa et al. | |
| 2003/0209792 | A1 | 11/2003 | Takaishi | |
| 2005/0082684 | A1 | 4/2005 | Aiba et al. | |
| 2005/0161818 | A1 | 7/2005 | Basceri | |
| 2006/0273304 | A1 * | 12/2006 | Cok | 257/40 |
| 2010/0184285 | A1 | 7/2010 | Hua et al. | |

FOREIGN PATENT DOCUMENTS

JP   2006-051164   * 2/2006

OTHER PUBLICATIONS

Zrenner, Eberhart et al., "Subretinal electronic chips allow blind patients to read letters and combine them to words," Proceedings of the Royal Society B, 2011, 278, 1489-1497, downloaded from http://rspb.royalsocietypublishing.org/, Jul. 18, 2011.

Shire, Douglas B. et al., "Development and Implantation of a Minimally Invasive Wireless Subretinal Neurostimulator," IEEE Transactions on Biomedical Engineering, vol. 56, No. 10, Oct. 2009.

(Continued)

*Primary Examiner* — Carl Arbes
(74) *Attorney, Agent, or Firm* — Blakely Sokoloff Taylor & Zafman LLP

(57) ABSTRACT

Methods and apparatuses for assembly of a non-planar device based on curved chips are described. Slots may be created as longitudinal openings in the chips to reduce bending stresses to increase allowable degrees of deformation of the chips. The chips may be deformed to a desired deformation within the allowable degrees of deformation via the slots. Holding constraints may be provided on at least a portion of the chips to allow the chips to remain curved according the desired deformation.

17 Claims, 12 Drawing Sheets

(56) References Cited

OTHER PUBLICATIONS

Ahuja, A. K., et al., "Blind subjects implanted with the Argus II retinal prosthesis are able to improve performance in a spatial-motor task," British Journal of Ophthalmology, 95:539-543, Sep. 29, 2010, downloaded from http://bjo.bmj.com/, Jul. 28, 2011.

Fan, L.-S. et al., "Monolithically Integrated Flexible Artificial Retina Microsystems Technology and in vitro Characterization," Association for Research in Vision and Ophthalmology, ARVO 2010, May 2-6, 2010, Ft. Lauderdale, Florida, USA, abstract.

Fan, Long-Sheng et al., "A Flexible & Translucent CMOS Retinal Prosthesis and in vitro Characterization," Association for Research in Vision and Ophthalmology, ARVO 2011, May 1-5, 2011, Ft. Lauderdale, Florida, USA, abstract.

Fan, L.-S. et al., "A Flexible Sensing CMOS Technology for Sensor-Integrated, Intelligent Retinal Prosthesis," Asia-Pacific Conference on Vision, APCV 2010, Jul. 23-26, 2010, Taipei, Taiwan, abstract.

Ng, David C. et al., "Impantable Microimagers," Sensors 2008, 8(5), 3183-3204, May 15, 2008.

Tokuda, Takashi et al., "Flexible and extendible neural interface device based on cooperative multi-chip CMOS LSI architecture," Sensors and Actuators A 122 (2005), 88-98, May 25, 2005.

International Search Report and Written Opinion mailed Jul. 6, 2012, for International Patent Application No. PCT/US2011/064014, 18 pages.

\* cited by examiner

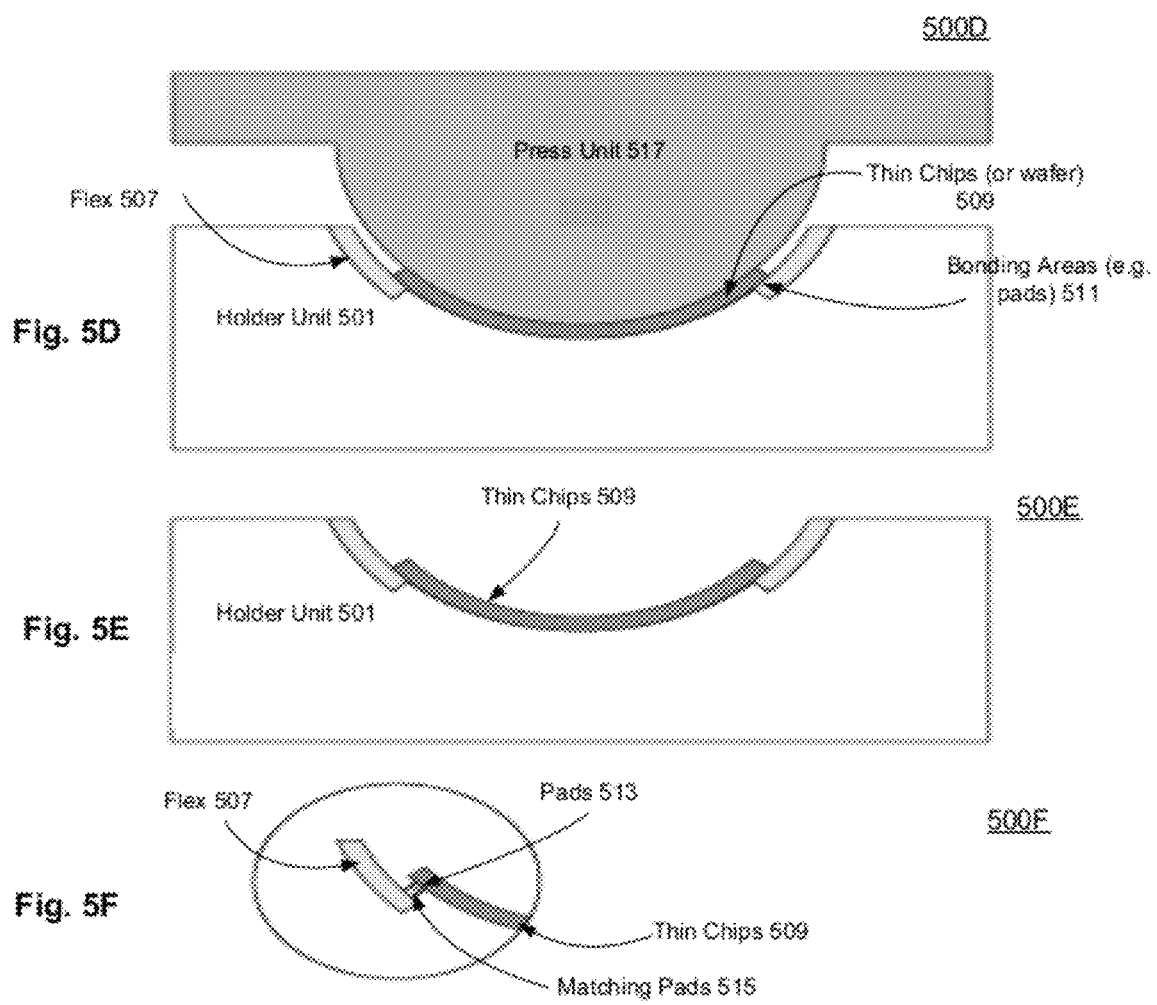

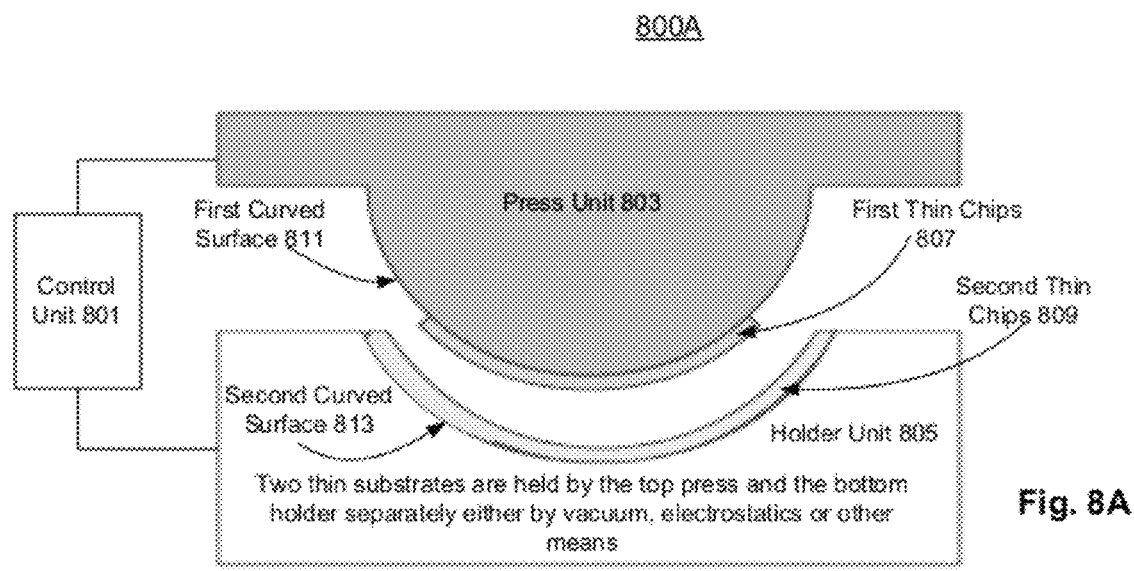
Fig. 8A
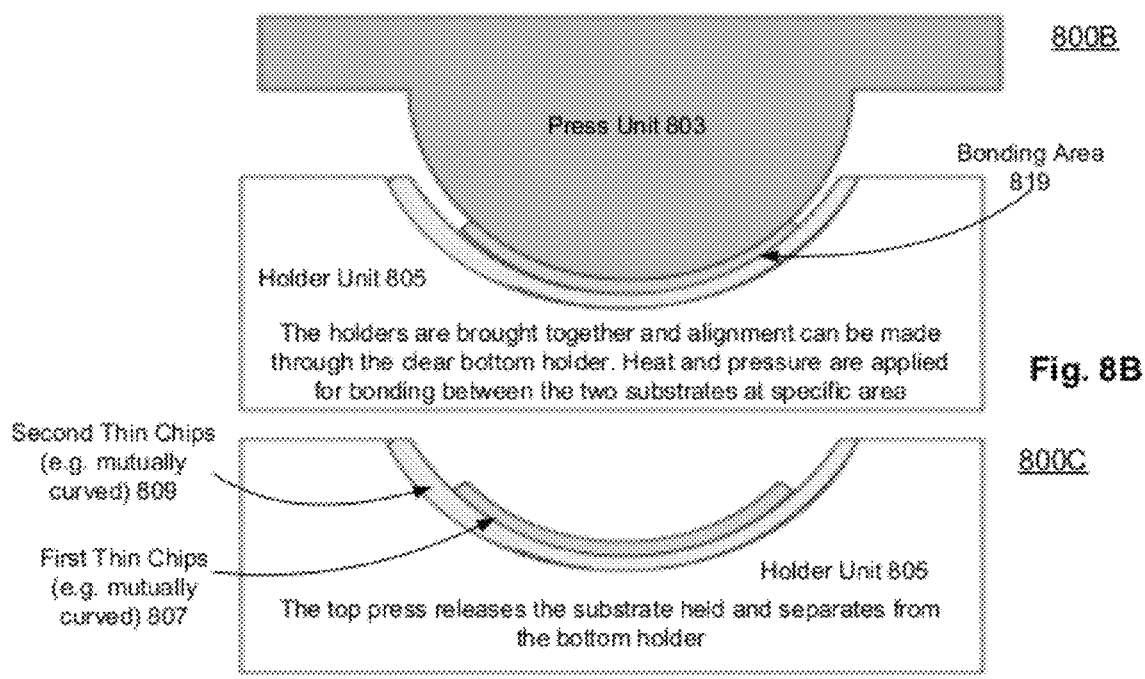
Fig. 8B
Fig. 8C

METHOD FOR NON-PLANAR CHIP ASSEMBLY

CLAIM TO PRIORITY

The present application is a continuation in part application of U.S. patent application Ser. No. 13/282,422 filed on Oct. 26, 2011, which is a continuation in part application of U.S. patent application Ser. No. 13/102,596 filed on May 6, 2011. The present application also claims the benefit of Provisional Patent Application No. 61/553,919, filed on Oct. 31, 2011. These applications are hereby incorporated by reference in their entirety into this application.

FIELD OF INVENTION

The present invention relates generally to assembly process of micro devices, and more particularly to assembly of three-dimensional curved flexible device chips.

BACKGROUND

Integrated electronic circuit (IC) industry relies on "planar" technology to reduce the limit of feature size of photolithography and to progress according to Moore's law, since the depth of focus is reduced when the numerical aperture is increased to define finer features in photolithography. However, planar surfaces of devices based on such planar technologies may limit geometry of interactions and/or interconnections among these devices or with an external system or external systems.

Thus, traditional planar technologies may not be capable of providing devices with non-planar geometries to minimize complexity of interactions among the devices or with external systems.

SUMMARY OF THE DESCRIPTION

In one embodiment, an assembly method for non-planar (e.g. quasi-spherical) structures, such as non-planar surface patch of a semiconductor chip (or chip stack) may comprise depositing stressed films on either side (or both sides) of a thin semiconductor substrate of a thin chip for small deformations of the chip. Stressed films may be deposited with patterning of the stressed films (for example, by using photolithography and etching or lift-off process) for small deformations with controlled shapes. Alternatively, slots may be created on thin chips and stressed films may be deposited to allow large deformation of the chip.

In another embodiment, "slots" may be created on thin chips and the chips may be bonded to a separate piece of a constraining element (for example, a ring-shaped patch or another chip) to allow larger deformation of the chips. The "slot" can be formed by continuous opening with varying width extended from a location within the chip to a chip edge that creates new straight or curved edges and sidewalls for the local structure and allows certain lateral displacements when the local structure is under bending or deforming stresses. The bonding may be mechanically constraining and optionally providing electrical connections between bonded pieces of elements across slots (including the chips). A combination of slots with stressed films and constraining elements can form a curved surface for the chips. Two or more slotted pieces of the chips may be bonded to have mutual or multiple constraints to hold curved pieces in place. In some embodiments, curved structures thus formed may be suitable for brain-machine interfaces (such as retinal prosthesis), or new architectures of 3D (three dimensional) interconnections of signal processing units.

An embodiment of the present invention includes methods and apparatuses for assembly of a non-planar device based on curved chips. Slots may be created as longitudinal openings in the chips to reduce bending stresses to increase allowable degrees of deformation of the chips. The chips may be deformed to a desired deformation within the allowable degrees of deformation via the slots. Holding constraints may be provided on at least a portion of the chips to allow the chips to remain curved according the desired deformation.

In another embodiment, curved chips can include multiple chips. One chip (e.g. a first one of the chips) may be curved to a desired deformation. Another chip (e.g. a second one of the chips) may be deformed to conform to the desired deformation of the first chip. The deformed chips may be bonded with each other with a continuous piece of one chip across the slot of another chip to provide holding constraints between these chips to allow these chips to remain curved in the desired deformation.

In yet another embodiment, an assembly apparatus for non-planar curved chips may comprise a set of pressure units, a holder unit and a control unit. The pressure units may have a first surface curved according to a desired curvature. The holder unit may have a second surface curved conforming to the desired curvature. The control unit may control movement of the pressure unit and the holder unit. The pressure unit may be configured to deform the chips to the desired curvature over the first surface. The holder unit may be configured to deform fixture structures according to the desired curvature over the second surface. The control unit may be configured to cause the pressure unit and the holder unit to bond the chips with the fixture structures between the first surface and the second surface via the movement of the pressure unit. The bonding may provide holding constraints for the chips and the fixture structures to remain curved.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which:

FIGS. 5A-5F are block diagrams illustrating an exemplary sequence of assembly process for a non-planar flexible device;

FIGS. 8A-8C are block diagrams illustrating an exemplary sequence to assemble curved stack of thin dies/wafers in one embodiment described herein.

DETAILED DESCRIPTION

Figure 1A:
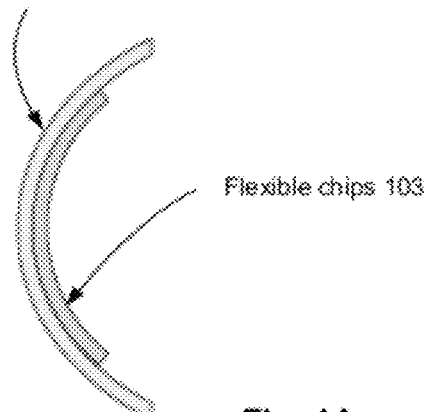
FIGS. 1A-1D are schematic diagrams illustrating exemplary embodiments of non-planar assembly for flexible chips.

Retina chip assembly processes or non-planar (such as quasi-spherical) surface patches of (integrated) semiconductor chips and methods are described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

In one embodiment, it is advantageous to have non-planar surfaces of integrated active devices, transistor circuits, transducers or micro systems, to change the geometry of interactions, interconnections among these devices, sub-systems, or interactions, interconnections with an external system, or external systems. Integrated devices with non-planar shapes or geometries may enable new computational architectures (such as a ball-shaped geometry is a "round-table forum" in 3D optimizing the interactions, communications, and interconnections between computational elements on the surfaces, and communication/interaction link inside the sphere). It enables new ways of interfacing electronics or photonics to biological neural systems in general (such as in the brain-machine interface (BMI), quasi-spherical surfaces are frequently encountered).

For example, in the case of an artificial retina, the interface between the prosthesis device and the retina at the back of a human eyeball is a quasi-spherical surface with a radius of curvature of ~12.5 mm. To minimize the complexity of interconnections through eyeballs, it is desirable to collocate the interfacing micro electrodes and electronic circuitry, and together in close proximity to the surface of retina neurons. This disclosure teaches the method to form the typically rigid semiconductor electronics into the non-planar (here, quasi-spherical) shape.

FIGS. 1A-1D are schematic diagrams illustrating exemplary embodiments of non-planar assembly for flexible chips. Assembly 100A of FIG. 1A may illustrate an artificial retinal prosthesis device in a quasi-spherical shape conforming to the shape of the retina in an eyeball to allow the device positioned in close proximity to the surface of retina neurons. The conformity of the shape thus may reduce the required electrical excitation thresholds of neurons and increases the granularity of the interface between the device (e.g. via electrodes) and the retina neurons.

In one embodiment, assembly 100A may comprise flexible chips 103 with light sensors, electrodes, driving circuits, etc. Flexible chips 103 may be mechanically constrained to be curved in a desired shape or deformation via fixture structure 101. For example, fixture structure 101 may comprise a flexible polymer material shaped or deformed with a desired curvature. Flexible chips 103 may be bonded or fixed to fixture structure 101 to remain curved in the desired shape.

Figure 1B:
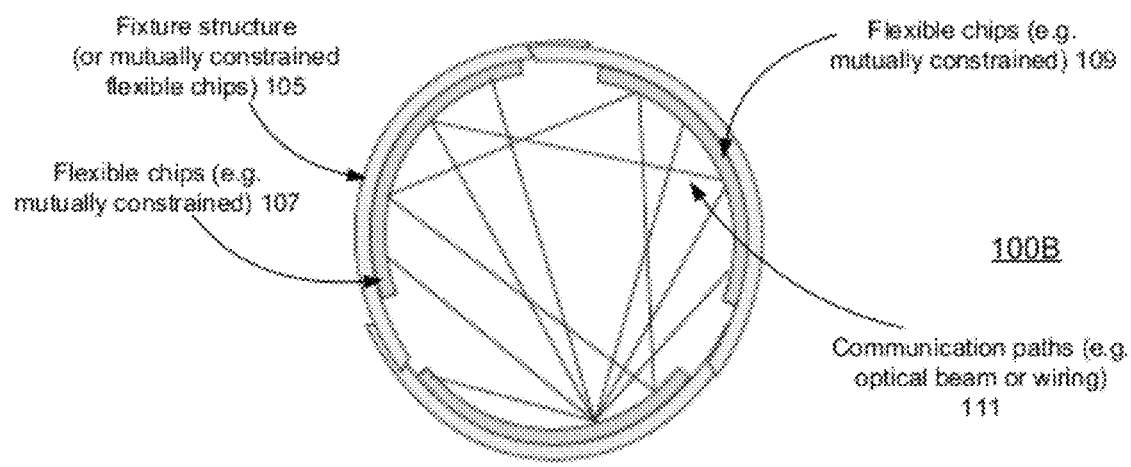

Turning now to FIG. 1B, assembly 100B may be a relatively spherical-shaped assembly comprising multi-layers of flexible chips. For example, flexible chips 107, 109 may be deformed to facilitate communications among surface elements of the chips 107, 109. Chips 107, 109 may be positioned or configured to face each other to establish communication paths, such as communication path 111, using either optical beams, wirings or other applicable connections. In some embodiments, a communication path between different curved chips facing in the same direction (such as ships 105, 107) may be based on through-silicon via. The through silicon via may bring some pads of a thin IC chip through its thin silicon substrate to the backside (e.g. from front side) of the thin IC chip so multiple chips can be stacked and bonded together. Multiple chips, such as fixture structure 105, flexible chips 107, may remain curved in assembly 100B based on mutual constraints between these chips.

The non-planar geometry of assembly 100B may enable computational architectures based on connections or other applicable non-planner shaped features. For example, a ball-shaped geometry in a sphere assembly may be a "round-table forum" in 3D (three dimensional) geometry for optimizing the interactions, communications, and interconnections between computational elements (or circuitry of flexible chips) on the surfaces of the sphere assembly, and communication/interaction links for elements located inside the sphere assembly.

Figure 1C:
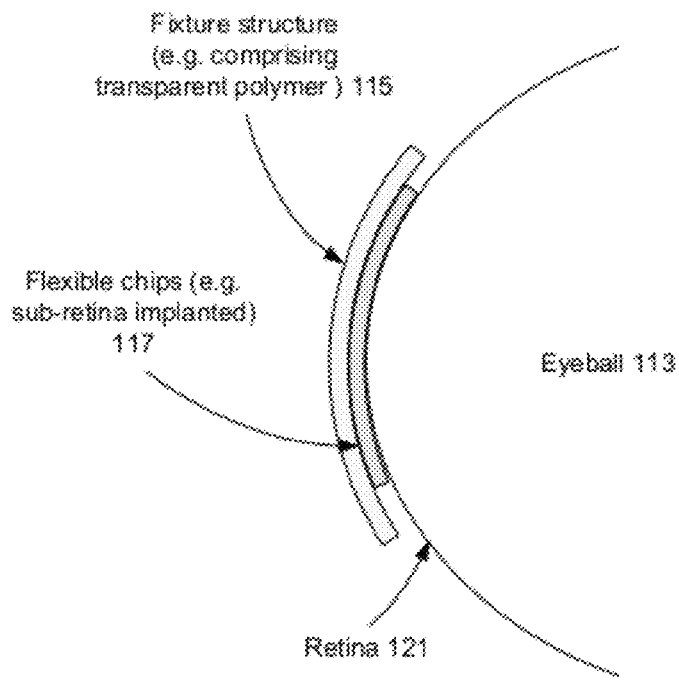

Turning now to FIG. 1C, a non-planar artificial retina assembly may be implanted for eyeball 113 in a sub-retina manner. The artificial retina may include flexible chips 117 in close contact with retina 121 of eyeball 113. Flexible chips 117 may be bonded with fixture structure 115 to remain curved to conform to the shape of eyeball 113. In one embodiment, both fixture structure 115 and flexible chips 117 may comprise transparent material to allow light to pass through.

Figure 1D:
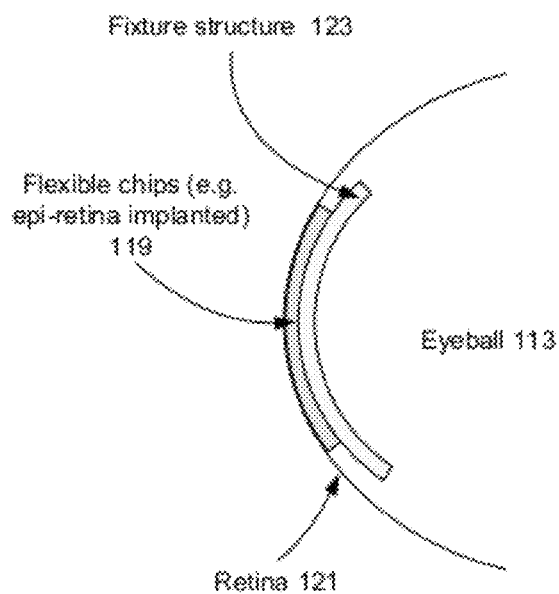

Alternatively, in FIG. 1D, a non-planar artificial retina assembly may be implanted for eyeball 113 in an epi-retina manner. The artificial retina may include flexible chips 119 in close contact with retina 121 from inside of eyeball 113. In addition, the artificial retina may include fixture structure 123 to provide mechanical constraints to allow flexible chips 119 to remain curved conforming to the shape of eyeball 113. The non-planar artificial retina assembly may be flexible so as to be deformed according to various configurations or shapes desired.

Figure 2A:
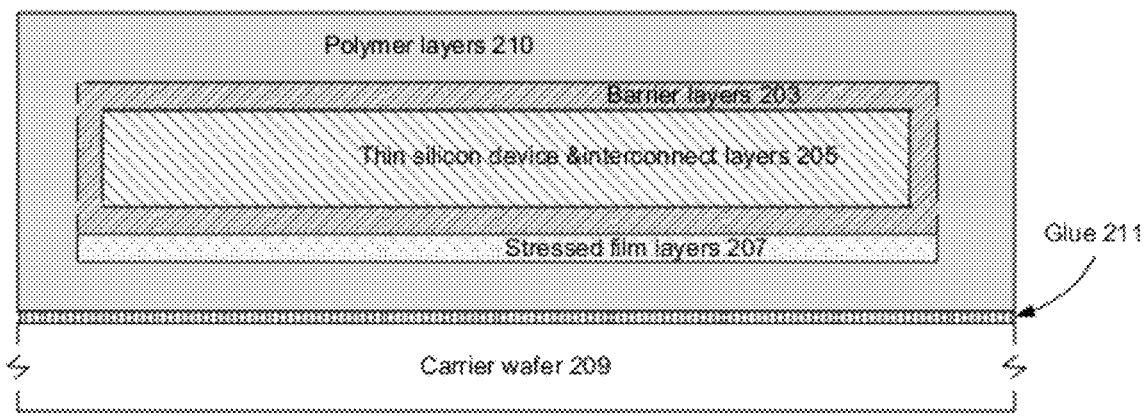
FIG. 2A is a block diagram illustrating cross sectional views of a flexible structure deposited with a stressed thin film according to embodiments described herein.

FIG. 2A is a block diagram illustrating cross sectional views of a flexible structure (or device) deposited with a stressed thin film. In one embodiment, structure 200 may include thin device layers 205 sandwiched between barrier layers 203 and polymers 210. Device layers 205 may be based on a thin MOS (Metal Oxide Semiconductor) die intended for medical implant wrapped by barrier layers 203 and biocompatible polymer layers 210 to protect against device corrosion and/or poisoning living tissues. Structure 200A may be thin enough to curl (or bend, deform) according to stress or stretching force from stressed film layers 207.

In some embodiments, stressed thin films, such as stressed film layers 207, may be deposited in either side or both sides of a thin structure or chip to achieve desired deformation (e.g. with a certain degrees bending) for the chip. For example, stressed thin films may be pre-compressed or pre-stretched to apply bending force in different directions. Optionally, stressed thin films can be patterned (for example, in annular shapes or long stripes by photolithography and etching processes) during the fabrication process to create various curved shapes (e.g. in a wavy manner or other applicable forms) for the thin structure. Structure 200 may curl when released from thick carrier wafer (or handle wafer) 209 attached via glue 211.

Figure 2B:
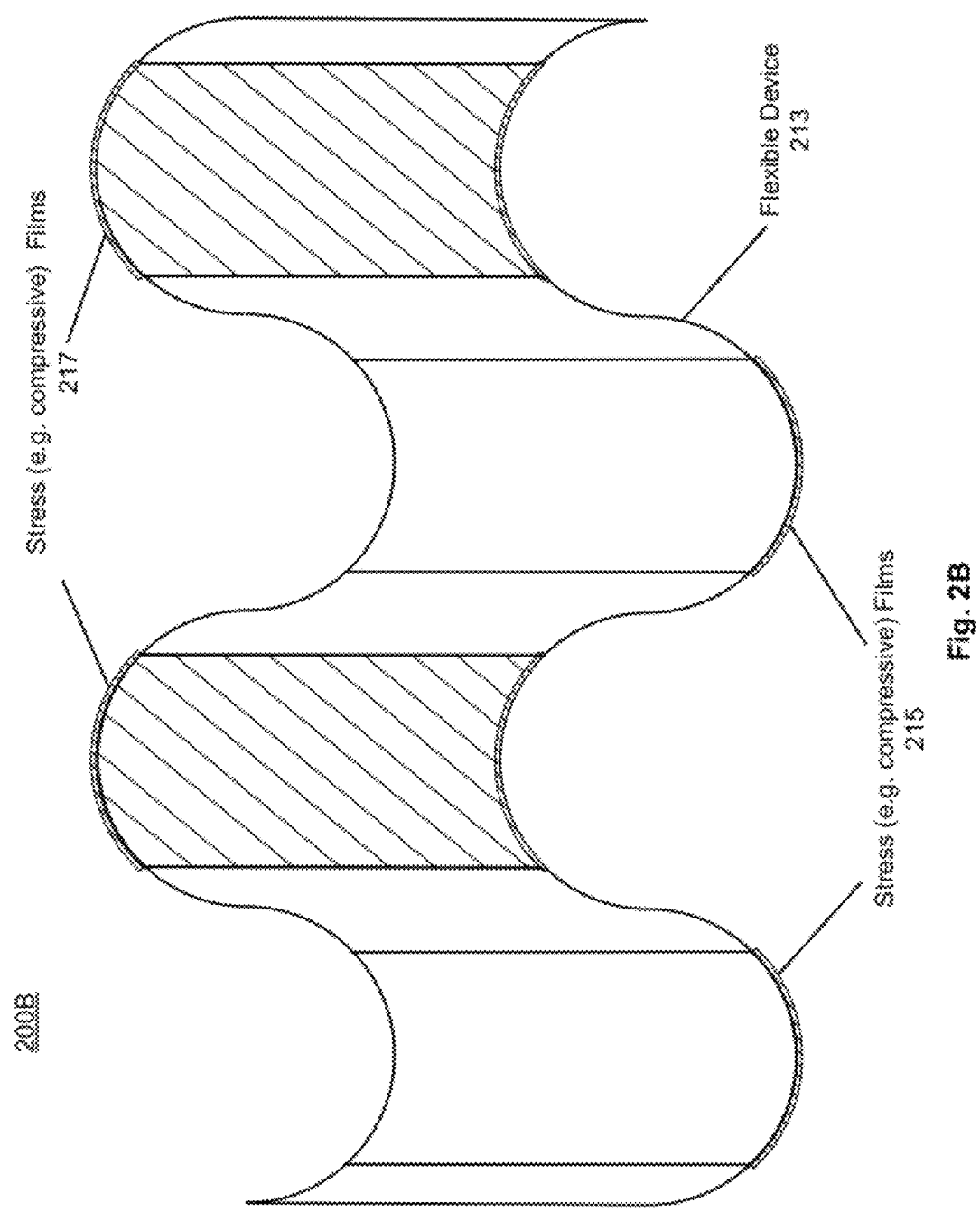
FIG. 2B is a schematic diagram illustrating a non-planar device deformed in a wavy manner according to embodiments described herein.

FIG. 2B is a schematic diagram illustrating a non-planar device deformed in a wavy manner according to embodiments described herein. For example, non-planner integrated circuit device 200B may include a flexible thin structure 213 curved in a wavy manner. Stressed films 215, 217 may be formed (e.g. via pattern masks) on both sides of structure 213 to form a specific (or pre-designated) pattern (e.g. stripes, zigzag, or other applicable patterns etc.) to curve structure 213 in a desired deformation, such as a wavy manner. In one embodiment, stress film 215 may be pre-compressed or compressive. Alternatively, stress films may be pre-stretched. Stress films 215,127 may provide displacement constraints or force, such as large residual thin film stresses, to curve the flexible structure 213 in the desired deformation. A non-planar device may include a combination of pre-compressed, pre-stretched, or compressive films formed in a designated pattern to provide stress distributions according the designated pattern to achieve desired deformation of the device.

According to one embodiment, desired deformation may include chip bending curvature. For example, if flexible chips are to be deformed into a non-planar spherical patch from a planar disk, the required reduction in the circumference of the outer circle of the flexible chips can be calculated. In one embodiment, estimation of the chip bending curvature caused by deposited thin films with residual film stresses (on a relatively thick substrate) may be based on "Stoney Equation" (or approximation equation) when the displacement from the substrate bending is much less than the wafer thickness (e.g. thickness of device layers 205). For larger stresses on thin chips, numerical methods may be used to calculate the chip bending curvature without over-estimating the displacement via the approximation equation, as the displacement can easily be larger than the substrate thickness due to two-dimensional constraints.

Figure 3A:
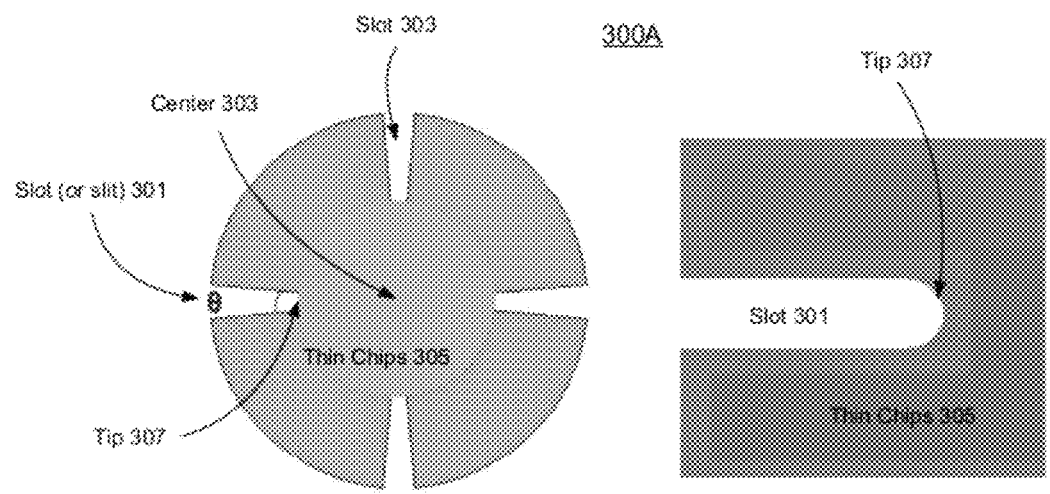
FIGS. 3A-3C are schematic diagrams illustrating exemplary non-planar chips based on slots according to embodiments described herein.
Figure 3B:
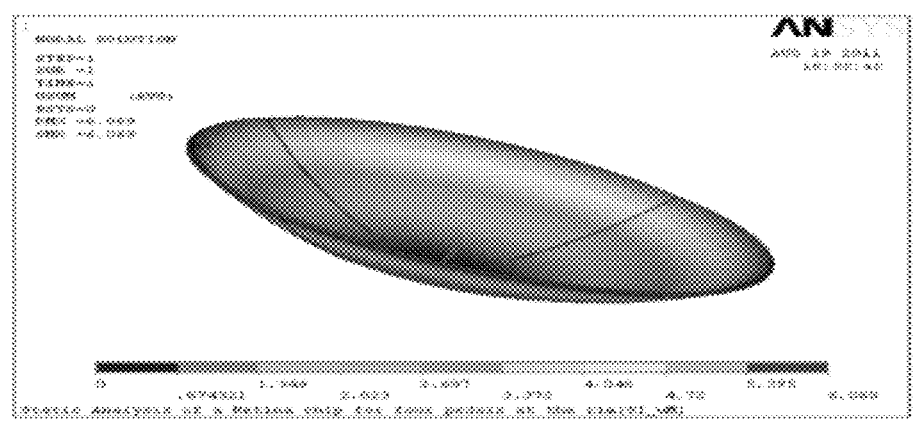
Figure 3C:
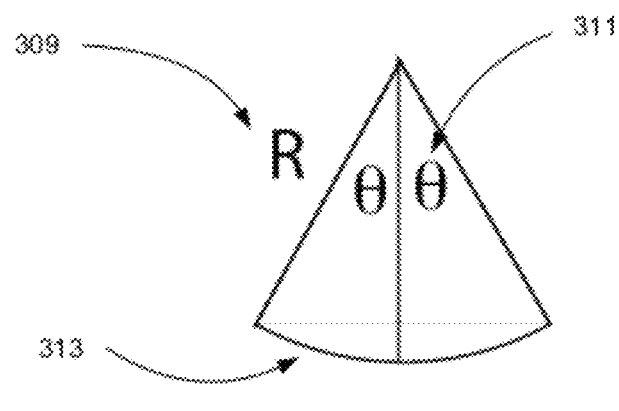

FIGS. 3A-3C are schematic diagrams illustrating exemplary non-planar chips based on slots according to embodiments described herein. For example, schematics 300A may include thin chips 305 of a thin die or wafer and exaggerated slot 301 with stress-relieve round corners at tip 307. When thin chips 305 is deformed, two sides of slot 301 may meet or close up. Thin chips 305 may be pre-stressed on a carrier substrate during fabrication process and become curved when released from the carrier substrate.

In one embodiment, thin chips 305 may comprise a circular chip with several radial slots (one or more) extending outward in the direction from the center of the circular chip (in a straight path or in a curved path, a spiral path, a zigzag path or other applicable paths) in fan/wedge shape with the surplus perimeters removed. The radial slots may extend from perimeter of thin chips 305 and stop at tips (e.g. fine tip about 1 µm in width) of the slots, such as tip 307 for slot 301, before (or at a distance from) reaching the center of thin chips 305. In one embodiment, tips of slots may be located within a thin chip to accommodate, for example, resolution limitation of micro fabrication process and/or increased stress intensity factors at the tip of the slot induced by chip deformation. Corners around tips of slots, such as around tip 307 of slot 301, may be rounded to reduce stress concentration associated with sharp corners and spread out stress over rounded slot corners when an associated chip is deformed or bended.

A slot may be formed by removing (or cutting, slitting), such as through deep reactive ion etching in the micro fabrication process, a portion of narrow channel area (e.g. a cutout, a longitudinal opening or narrow opening) of a chip, such as slot 301 of thin chips 305. The slot can reduce deformation stress, such as tangential in-plane stress, of the chip and increase allowable degrees of deformation of the chip. In one embodiment, the slot may break direct communication, within the chip, between circuit elements crossing the slots, thus jumpers (through the bonding pads to the constraining flex or another constraining chip, as will be described in the following), or longer power rails and data buses around the slots may be needed to distribute the power, ground & signal lines.

FIG. 3B shows a layered thin disk chip structure fabricated with slots and stressed films to bend or curve into a quasi-spherical patch and remain curved after release from a carrier wafer used during fabrication. Fixture structures may be bonded across the slots in the chip structure to prevent the curved chip from relaxing back to its original planar shape. The stress film may provide additional bending force to help constrain the chip to remain in a desired deformation. Although bending effect from stressed thin films on thin structures with one or more slots can greatly increase, large bending (e.g. 70-90 microns of edge displacement in the bending of a 30-micron thick retinal chip) may be associated with two dimensional constraints. Degrees of deformation may be measured, for example, in micros of edge displacement. As a result, relatively thicker films with large stresses (e.g. external bending) may be needed to achieve the desired large curvature.

FIG. 3C illustrates exemplary mechanisms to curve a planar chip. When a planar disk (e.g. including a planar chip) of diameter "d" is bent into a radius of curvature "R" 309, the angle 311 extended from the center of radius to the end points of a diameter line of the disk is $2\theta$, where $2R*\theta=d$. The original circumference of the disk is $S=\pi*d=2\pi R*\theta$; however, the deformed circumference 313 should be $S'=2\pi R*\text{Sin}(\theta)$ if the disk is deformed into a patch of a spherical shape. Since $\theta > \text{Sin}(\theta)$ when $\theta > 0$, the disk will experience in-plane tangential compressive stresses against the bending since there are excess of circumference $2\pi r*[\theta - \text{Sin}(\theta)]$ at a radius r less or equal R. The slots remove such excess in an appropriate amount such that the two edges of the slot is brought together when the disk is deformed into a spherical shape. This principle of removing certain excess material from a planar chip into a curved non-planar shape may be applicable in some embodiments described herein.

Figure 4A:
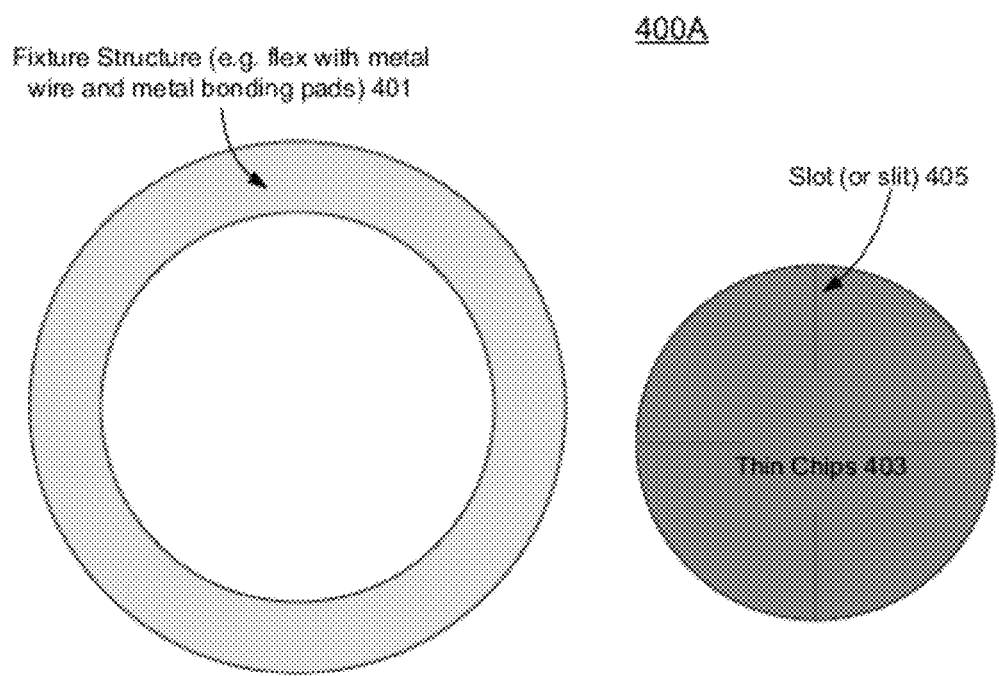
FIGS. 4A-4B are schematic diagrams illustrating exemplary embodiments of a thin chip assembled with a flex.
Figure 4B:
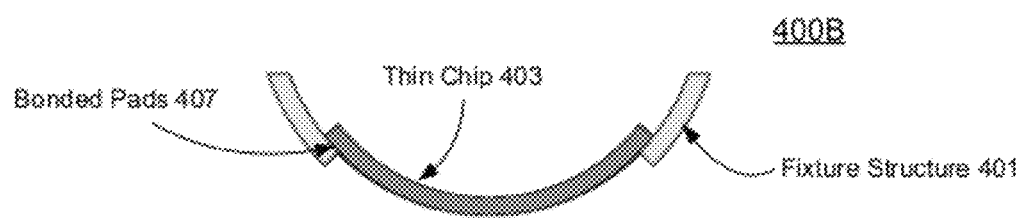

FIGS. 4A-4B are schematic diagrams illustrating exemplary embodiments of a thin chip assembled with a flex. Schematic 400A may include fixture structure 401 and thin chips 403. In one embodiment, fixture structure 401 may be a flex shaped in an annular ring (for example, formed from a flex "cable"). A flex may comprise a polymer (e.g. Polyamide) which can be transparent or translucent, deformable and/or moldable. In some embodiments, a flex may be shaped as a whole piece or in different applicable shapes according to desired deformation required. Thin chip 403 may be based on a thin wafer/die with slits for large deformation. In one embodiment, thin chips 403 may comprise flexible material with four slits (or slots), such as slot 405, to increase flexibility of the chip for large deformation. Fixture structure 401 may be bonded to flexible thin chip 403 to keep the chip in a bending state. The number and/or pattern of slots (e.g. 2, 12 or other applicable number of slots) formed on a thin chip may vary depending on desired deformation in the chip Turning now to FIG. 4B, assembly 400B may include curved thin chips 403 bonded with fixture structure 401 via, for example, bonded pads 407. Mechanical constraints from fixture structure 401 (or flex) may keep thin chips 403 to remain curved without relaxing back to its original flat state. Fixture structure 401 may include metal wires and metal bonding pads with appropriate thickness (for example, ~10 µm). Thin chips 403 may include matching (in relative location) bonding pads to be bonded with corresponding metal bonding pads of fixture structure 401. The metals may form thin-film bonding (for example, Au to Au) when under a pressure force in an elevated temperature (typically controlled within a range of 150 degree C. to 450 degree C.). The thin film bonding can also be used as electrical connections for data communication and power distribution.

FIGS. 5A-5F are block diagrams illustrating an exemplary sequence of assembly (or joining) process for a non-planar flexible device. For example, the non-planar flexible device may be fabricated or manufactured based on a curved thin wafer/die bonded with the flexible device via matching pads. At sequence 500A of FIG. 5A, in one embodiment, holder 501 may comprise a clear holder with recessed shapes, such as recess 503, to accommodate a flex or fixture structure. Recess 503 may accommodate flex material (e.g. polymer) which can be molded or shaped.

Figure 5A:
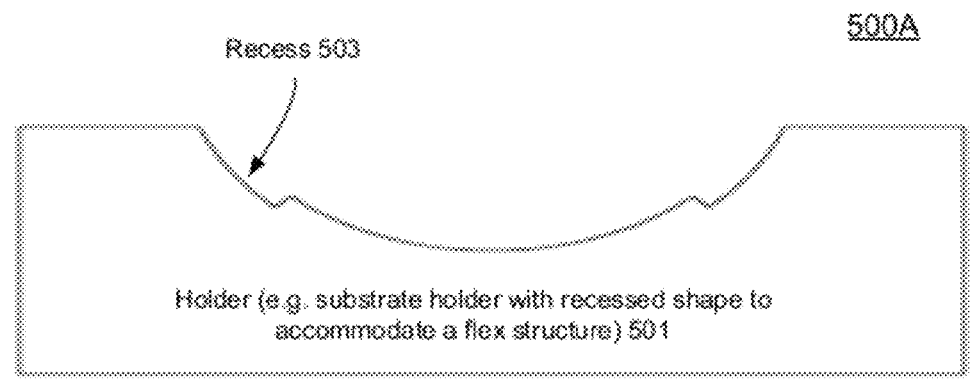
Figure 5B:
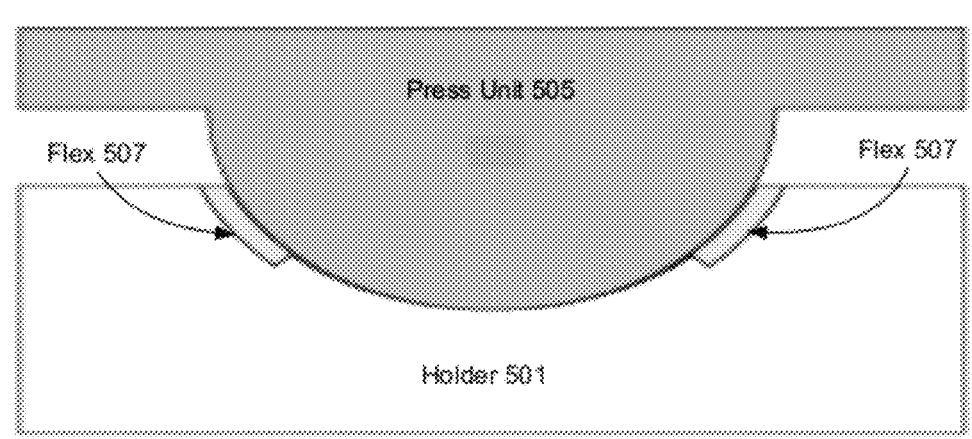
Figure 5C:
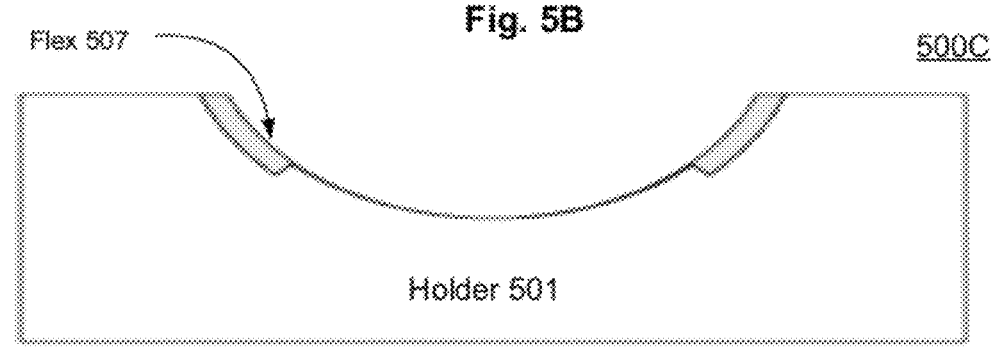

At sequence 500B of FIG. 5B, flex 507 may be tooled in recess 503. In one embodiment, press unit 505 and holder unit 501 may be brought together with pressure/heat applied to form flex 507 into a curved shape. Press unit 505 and holder unit 501 may be shaped with matching surfaces having a common or compatible radius of curvature. Flex 507 may be sandwiched between a press unit 505 (e.g. top unit) with spherical surface and holder unit 501 (e.g. bottom unit) with matching spherical recess. In one embodiment, flex 507 may comprise a polymer based ring held by vacuum (with vacuum holes on the surface of corresponding area, and vacuum channels inside holder 501) or by electrostatic force (e.g. using an electrostatic chuck). At sequence 500C of FIG. 5C, press unit 505 may be moved to separate from the holder unit 501 and leave flex 507 to remain deformed (or molded) in place (e.g. in recess 503). In some embodiments, thin chips bonded with a flex may be deformed based on mutual constraints between the flex and the thin chips without a need to mold the flex.

Turning now to FIG. 5D, at sequence 500D, press unit 505 and holder unit 501 may be brought together for bonding between thin chips (or wafer) 509 and flex 507 after press unit 517 and holder unit 501 are aligned. For example, thin chips 509 may be bonded or jointed with flex 507 at specific areas, such as bonding areas 511. Thin chip 509 may include metal based pads. Correspondingly, flex 507 may include matching pads. In one embodiment, press unit 505 may be aligned (e.g. via three dimensional rotational movements) with holder unit 501 to allow pads of thin chips 509 in contact with corresponding matching pads of flex 507. At least one of press unit 505 and holder unit 501 may be clear to allow the alignment. Press unit 505 of FIG. 5B and press unit 517 may be part of a plurality of press units with surfaces curved in different curvatures in one common assembly apparatus for non-planar devices.

In one embodiment, heat and pressure may be applied for bonding between thin chips 509 and flex 507, for example, to solder metal pads and corresponding matching pads together. Thin chips may be held on press unit (e.g. top press) 505, for example, via vacuum or electrostatics forces. Press 517 may be pressed against holder unit 501 after alignment of pads of thin chips 509 and matching pads of flex 507.

In some embodiments, flex 507 may be made through a clear bottom holder such as holder 501. Multiple layers of chips may be bonded via pressure and heat applied between a press unit and holder unit 501. Holder unit 501 may be associated with different shapes or styles of recesses to deform a flex or flexible chips, such as flex 507, depending on different chip designs. When the bonding is completed, at sequence 500E of FIG. 5E, press unit 505 may move away from holder unit 501 to release thin chip 509 bonded with flex 507 in a non-planar shape. Bonding pads may harden when cool down from bonding pressure/heat to cause separate chips/wafers to stick together (or bonded) in a curved or non-planar shape. In one embodiment, thin chips 509 bonded with flex 507 may be passivated (or coated) with barrier layers and/or polymer layers (e.g. to protect against corrosion) subsequent to sequence 5E. Air gaps between flex 507 (e.g. a separate chip mutually constrained to remain curved) and thin chips 509 may be backfilled with thermal conducting dielectric material for increase heat dissipation capability.

FIG. 5F shows an exaggerated view of a bonding pad between thin chips 509 and flex 507. For example, pad 513 of thin chips 509 may be bonded (or soldered) with matching pads 515 of flex 507. Pads 513 and matching pads 515 may comprise the same or different conducting material (e.g. gold). Bonding contact of a non-planar device, such as pads 513 bonded with matching pads 515, may be covered or coated (e.g. vapor coating or vacuum coating) with thin layer of hard passivation made of silicon nitride, diamond carbon or other applicable material to provide insulation and prevent exposing the bonding contact of the device. In one embodiment, bonding contacts may provide mechanical joining constraints and/or optional electrical connections between different portions of curved chips.

Figure 6A:
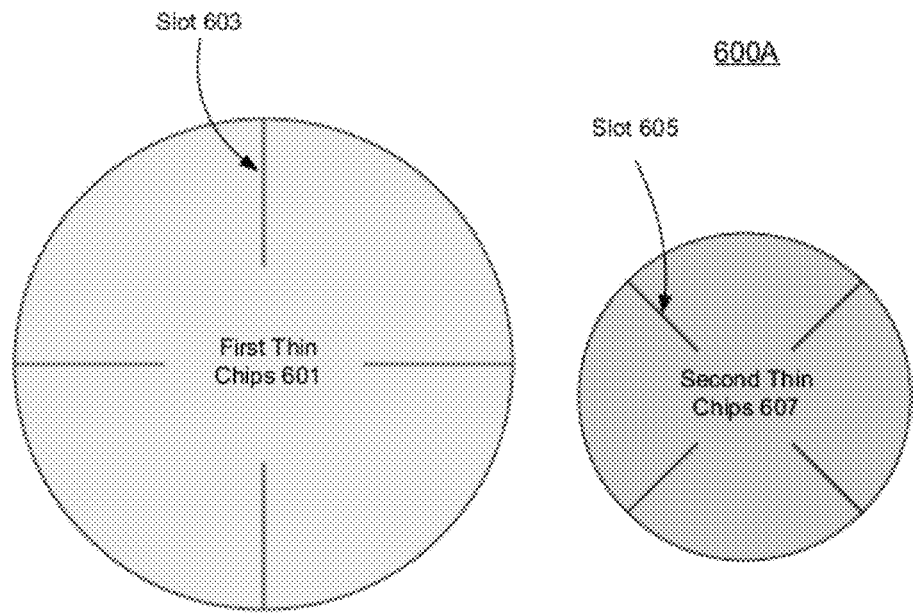
FIGS. 6A-6B are schematic diagrams illustrating exemplary embodiments of mutually constrained non-planar chips.
Figure 6B:
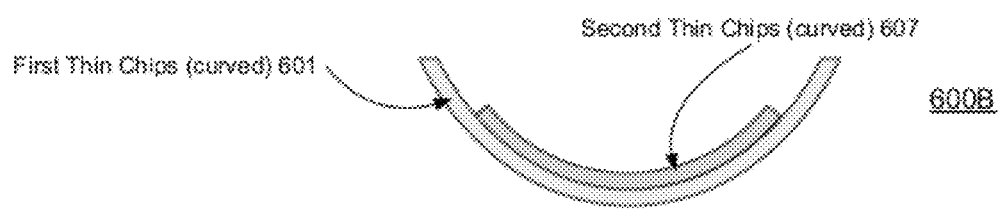

FIGS. 6A-6B are schematic diagrams illustrating exemplary embodiments of mutually constrained non-planar chips. For example, schematic 600A of FIG. 6A may illustrate two thin wafers/dies with off-set slits and matching bonding pads for mutual constraints for an assembly of curved chips. In one embodiment, first thin chips 601 and second thin chips 607 may each include four radial slots with matching metal bonding pads. Thin chips may be assembled with slots aligned with an angle. For example, slot 605 may cross slot 603 with a, for example, 45 degree angle in the assembled curved thin chips.

Turning now to FIG. 6B, assembly 600B may include first thin chips 601 and second thin chips 607 curved via mutual constraints. Assembled curved thin chips, such as first thin chip 601 and second thin chip 607, may not relax back to original flat or planar states because of mutual constraints applied to each other at bonding locations (e.g. bonding pad areas). In one embodiment, bonding pads may be paired across each slot of a thin chip to stick together portions of the chip across the slot.

Figure 7A:
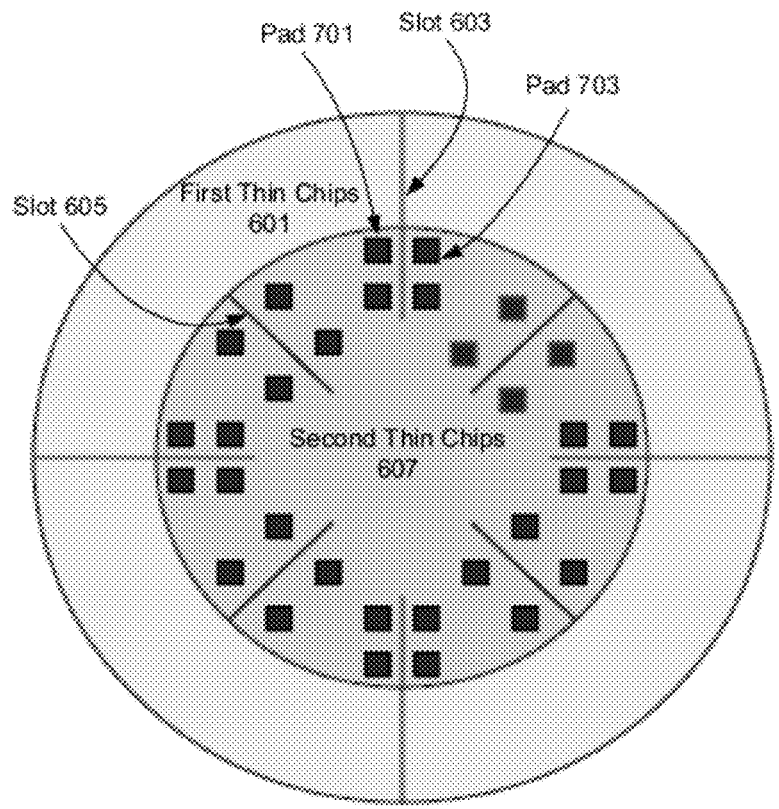
FIGS. 7A-7B are schematic diagrams illustrating exemplary top view and cross sectional view of an assembly with bonding pads.
Figure 7B:
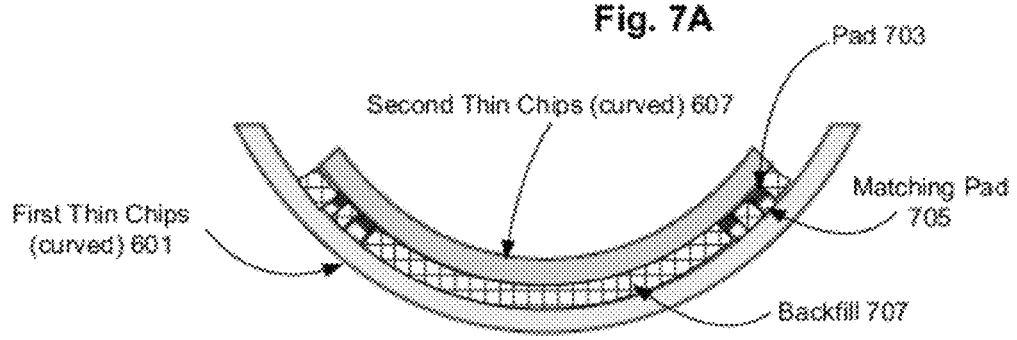

FIGS. 7A-7B are schematic diagrams illustrating exemplary top view and cross sectional view of an assembly with bonding pads. For example, FIG. 7A illustrates a top view of a non-planar 3D packaging of a stack of two thin chips, such as second thin chips 607 over first thin chips 601, curved into quasi-spherical shape. Neighboring slots between the stacked chips may be aligned with an angle (e.g. 45 degrees), such as slot 605 of second thin chips 607 and slot 603 of first thin chips 601. The bonding pads may be positioned on both sides of slots, such as pads 701 and pads 703 across slot 603.

FIG. 7B illustrates a cross sectional view (e.g. not to scale with exaggeration) of the thin film bonding with bond pads regions. For example, second thin chips 607 and first thin chips 601 may remain curved via bonding of pads, such as bonding between pad 703 and matching pad 705. Alternatively or optionally, thin chips may be bonded via glue to remain in a non-planar shape.

In one embodiment, a backfill layer, such as backfill 707, between adjacent chips of a non-planar assembly stacking multiple chips may facilitate heat dissipation between the chips. A backfill layer may comprise thermal conductive dielectric material to control the temperature rise of the assembled structure (or non-planar chips) in operation. For example, heat generated from high speed processing circuitry embedded inside a non-planar assembly may be allowed to pass through both bonding pads and backfill layers to help cool down the non-planar assembly. In one embodiment, a backfill layer may reduce or eliminate thermal insulation of air gaps in a non-planner assembly. Alternatively, the non-planar assembly may be immersed in a liquid, such as silicon oil, to fill up air gaps to provide cooling effects.

The stack is not limited to two layers, or limited to round shapes. Multiple chips non-planar 3D stack with staggered slots can be formed. Power, signals and data can jump between layers to cross the slots to distribute electrical power and signals between stacked pieces and adjacent pieces. Since the active devices will be under bending stresses, the stress-induced effects such as the increase of trans-conductance for tensile stresses in both longitudinal and transverse directions on N-type MOS transistors, and either increase or decrease in the case of P-type transistors may be taken into account and pre-compensated in the system design.

FIGS. 8A-8C are block diagrams illustrating an exemplary sequence to assemble curved stack of thin dies/wafers or substrates in one embodiment described herein. For example, at sequence 800A of FIG. 8A, two thin chips, first thin chips 807 and second thin chips 809, may be held in an assembly apparatus. In one embodiment, the assembly apparatus may include press unit 803 (e.g. upper unit), holder unit 805 (e.g. lower unit) and a control unit 801. Press unit 803 and/or holder unit 805 may move in a three dimensional manner including translational and/or rotational movements, for example, controlled by control unit 801.

In one embodiment, first thin chip 807 and second thin chip 809 may be separately held by press unit 803 and holder unit 805 either by vacuum, electrostatics or other means. For example, press unit 803 or holder unit 805 may comprise vacuum chucks with rings of small holes or openings of vacuum channels to provide suction forces to hold thin chips. Press unit 803 and holder unit 805 may be associated with matching surfaces to deform the thin chips held. In one embodiment, first thin chips 807, when held by press unit 803, may be deformed over first curved surface 811 of press unit 803. Second thin chips 809, when held by holder unit 805, may be deformed over second curved surface 813 of holder unit 805. First thin chips 807 and/or second thin chips 809 may include slots to increase flexibility of the chips to deform (or curve, bend). First curved surface 811 and second curved surface 813 may be of a common curvature to match each other.

At sequence 800B of FIG. 8B, holders may be brought together after alignment. For example, holder unit 805 may be clear or transparent to allow alignment with press unit 803 via first chin chips 807 and second thin chips 809. In one embodiment, alignment between holders may be based on matching corresponding bonding pads between first thin chips 807 and second thin chips 809 (e.g. based on masks).

Press unit 803 may rotate in three rotational dimensions for aligning chips held. In one embodiment, press unit 803 may be constrained to move in one translational dimension, for example, towards or away from holder unit 805, to allow surfaces of holders, e.g. first curved surface 811 and second curved surface 813, to match each other. In some embodiments, surfaces of the holders may match with a common center of curvature (or ball center).

As press unit 803 and holder unit 805 are brought together, heat and pressure may be applied for bonding between first thin chips 807 and second thin chips 809 at specific area of thin metal film bonding region, such as bonding area 819. Thin metal film bonding region may include pads aligned with matching pads between the thin chips. In one embodiment, pads may melt together using controlled ranges of elevated temperatures. For example, heat of about 100-180 degrees C. (Celsius) may be used for tin/lead based pads. Alternatively, heat of about 350-450 degrees C. may be needed for pads made of gold alloy.

At sequence 800C of FIG. 8C, press unit 803 may release first chips 807 held and separate itself from holder unit 805. A non-planar assembly including first chips 807 bonded with second chips 809 may remain curved via mutual constraints provided from established bonding between the chips.

In the foregoing specification, the invention has been described with reference to specific exemplary embodiments thereof. It will be evident that various modifications may be made thereto without departing from the broader scope of the invention as set forth in the following claims. The invention is not limited to the particular forms, drawings, scales, and detailed information disclosed. The specification and drawings are, accordingly, to be regarded in an illustrative sense rather than a restrictive sense.

What is claimed is:

1. An assembly method for a non-planar device based on one or more curved semiconductor chips, the method comprising:

slitting the chips to form a plurality of slots as cutout channel openings longitudinally over chip surfaces from perimeters of the chips, wherein deformation of the chips from planar shapes causes displacement stresses in the chips and wherein the slots reduce the displacement stresses;

deforming the chips with the slots to a predetermined deformation having a curvature over the chip surfaces; and providing holding constraints on at least a portion of the chips, the holding constraints to provide forces to allow the chips to remain deformed with the reduced displacement stresses according the predetermined deformation.

2. The method of claim 1, wherein the predetermined deformation corresponds to a quasi-spherical curvature conforming to a human eyeball.

3. The method of claim 1, wherein at least one of the chips is relatively spherically shaped with a perimeter having a center, wherein the at least one of the chips have one or more particular ones of the slots arranged in a radial pattern extended outwardly from the center to the perimeter.

4. The method of claim 3, wherein each of the particular slots is shaped as a channel area radiating from a stop distance to the center towards the perimeter, and wherein the creating the slots comprises:

cutting the at least one of the chips from the perimeter towards the stop distance of the center along the channel area.

5. The method of claim 4, wherein the stop distance is determined based on a finite resolution of an equipment for the cutting of the at least one of the chips.

6. The method of claim 4, wherein the cutting stops with fine tips at about the stop distance to the center of the chip, wherein the fine tips have sharp corners around the channel area, the method further comprising:

rounding the fine tips to form the slot shaped without sharp corners close to the distance to the center.

7. The method of claim 4, wherein cutting the at least one of the chips corresponds to an opening along the perimeter, wherein length of the opening is determined based on the predetermined deformation, and wherein the cutting the at least one of the chips comprises removing chip material.

8. The method of claim 1, wherein the deforming the chips comprises:
depositing stressed thin films over at least one side of the chips, the stressed thin films to provide a displacement force for at least a portion of the predetermined deformation.

9. The method of claim 8, wherein the stressed thin films are patterned to configure the displacement force.

10. The method of claim 1, wherein the predetermined deformation is configured via a curved surface of a holder, and wherein the deforming comprises:
pressing the chips over the curved surface of the holder to curve the chips for the predetermined deformation.

11. The method of claim 10, wherein the holder includes vacuum holes distributed over the curved surface and wherein the pressing is based on vacuum sucking force applied via the vacuum holes.

12. The method of claim 10, wherein the holder includes electrostatic chuck over the curved surface and wherein the pressing is based on electrostatic force applied via the electrostatic chuck.

13. The method of claim 1, wherein the chips include a plurality of pads, wherein the holding constraints mechanically constrain relative positions of the pads against one or more fixture structures, wherein providing holding constraints comprises:
forming the fixture structures shaped according to the predetermined deformation, the fixture structures including matching pads corresponding to the pads of the chips; and
bonding the pads with the corresponding matching pads while maintaining the chips shaped according to the predetermined deformation.

14. The method of claim 13, wherein bonding the pads comprises:
aligning the chips and the fixture structures based on the predetermined deformation; and
pressing the chips against the fixture structures within a controlled range of elevated temperatures.

15. The method of claim 13, wherein at least two of the pads are bonded to one of the fixtures, wherein the at least two pads are positioned across one of the slots, and wherein the holding constraints include constraints of the at least one fixture to maintain the predetermined deformation of the chips along the at least one slot.

16. The method of claim 13, wherein the fixture structures comprise flexible material, and wherein forming the fixture structure comprises:
molding the fixture structures conforming to the predetermined deformation using pressure force within a range of predetermined elevated temperatures.

17. The method of claim 1, wherein the fixture structures comprise separate chips and wherein the chips and the separate chips maintain curved according to the predetermined deformation via mutual constraints including the holding constraints by the fixture structures.

* * * * *